(12) United States Patent
Georgeson et al.

(10) Patent No.: US 7,313,959 B2
(45) Date of Patent: Jan. 1, 2008

(54) MAGNETICALLY ATTRACTED APPARATUS, SYSTEM, AND METHOD FOR REMOTE BONDLINE THICKNESS MEASUREMENT

(75) Inventors: Gary E. Georgeson, Federal Way, WA (US); Michael Fogarty, Auburn, WA (US)

(73) Assignee: The Boeing Company, Chicago, IL (US)

( * ) Notice: Subject to any disclaimer, the term of this patent is extended or adjusted under 35 U.S.C. 154(b) by 217 days.

(21) Appl. No.: 11/137,307

(22) Filed: May 25, 2005

(65) Prior Publication Data

US 2006/0266123 A1  Nov. 30, 2006

(51) Int. Cl.
*G01N 29/24* (2006.01)
(52) U.S. Cl. .............................. 73/620; 73/624; 73/635
(58) Field of Classification Search ................ 73/624, 73/634, 639, 643, 640, 641, 644, 622, 866.5, 73/620, 635
See application file for complete search history.

(56) References Cited

U.S. PATENT DOCUMENTS

| | | | |
|---|---|---|---|
| 4,010,636 A | | 3/1977 | Clark et al. |
| 4,117,733 A | | 10/1978 | Gugel |
| 4,466,286 A | | 8/1984 | Berbeé et al. |
| 4,612,808 A | | 9/1986 | McKirdy et al. |
| 4,807,476 A | | 2/1989 | Cook et al. |
| 5,062,301 A | | 11/1991 | Aleshin et al. |
| 5,311,785 A | * | 5/1994 | Bar-Shay .................... 73/866.5 |
| 5,665,896 A | * | 9/1997 | McMurtry ................... 73/1.75 |
| 5,902,935 A | | 5/1999 | Georgeson et al. |
| 6,167,110 A | | 12/2000 | Possin et al. |
| 6,424,150 B2 | * | 7/2002 | Kwun et al. ................. 324/216 |
| 6,484,583 B1 | | 11/2002 | Chennell et al. |
| 6,507,635 B2 | | 1/2003 | Birdwell et al. |
| 6,539,642 B1 | * | 4/2003 | Moriyasu et al. .............. 33/551 |
| 6,552,803 B1 | * | 4/2003 | Wang et al. ................. 356/503 |
| 6,658,939 B2 | | 12/2003 | Georgeson et al. |
| 6,711,235 B2 | | 3/2004 | Galish et al. |

(Continued)

FOREIGN PATENT DOCUMENTS

EP  1 193 491 A2  4/2002

(Continued)

OTHER PUBLICATIONS

*Inspection of In-Service Composite-Honeycomb Structures*, Aerospace Application Note, Rev.: Jan. 2002, R/D Tech.

(Continued)

*Primary Examiner*—Hezron Williams
*Assistant Examiner*—Jacques M. Saint-Surin
(74) *Attorney, Agent, or Firm*—Alston & Bird LLP

(57) ABSTRACT

Apparatus, systems, and methods for inspecting a structure are provided which use magnetically coupled probes disposed proximate opposite surfaces of a structure to locate, move, position, and hold a pulse echo ultrasonic transducer of one of the probes for non-destructive inspection, such as measuring a remote bondline thickness of a joint of a composite sandwich structure. The pulse echo ultrasonic sensor is included in a tracking probe, and the position of the tracking probe and pulse echo ultrasonic sensor are controlled by movement and positioning of a magnetically coupled driven probe in a leader-follower configuration. The tracking probe may be initially placed in a remote location using a detachable, and possibly deformable, placement rod.

24 Claims, 6 Drawing Sheets

U.S. PATENT DOCUMENTS

| | | | |
|---|---|---|---|
| 6,722,202 | B1 | 4/2004 | Kennedy et al. |
| 6,734,982 | B2 * | 5/2004 | Banet et al. ............... 356/630 |
| 6,748,791 | B1 | 6/2004 | Georgeson et al. |
| 7,093,491 | B2 * | 8/2006 | Murphy et al. ............... 73/620 |
| 2003/0154801 | A1 | 8/2003 | Georgeson |
| 2003/0210027 | A1 | 11/2003 | Pedigo et al. |
| 2004/0037393 | A1 | 2/2004 | Birdwell et al. |
| 2004/0103721 | A1 | 6/2004 | Georgeson |
| 2006/0053892 | A1 * | 3/2006 | Georgeson et al. ........... 73/634 |
| 2006/0055399 | A1 * | 3/2006 | Georgeson et al. ......... 324/232 |

FOREIGN PATENT DOCUMENTS

JP 9229911 A 9/1997

OTHER PUBLICATIONS

U.S. Appl. No. 10/752,890, filed Jan. 7, 2004, In re: Bossi et al., entitled *Non-Destructive inspection Device for Inspecting Limited-Access Features of a Structure.*

U.S. Appl. No. 10/943,088, filed Sep. 16, 2004, In re: Georgeson et al., entitled *Magnetically Attracted Inspecting Apparatus and method Using a Ball Bearing.*

U.S. Appl. No. 10/943,135, filed Sep. 16, 2004, In re: Georgeson et al., entitled *Magnetically Attracted Inspecting Apparatus and Method Using a Fluid Bearing.*

U.S. Appl. No. 10/943,170, filed Sep. 16, 2004, In re: Georgeson et al., entitled *Alignment Compensator for Magnetically Attracted Inspecting Apparatus and Method.*

* cited by examiner

MAGNETICALLY ATTRACTED APPARATUS, SYSTEM, AND METHOD FOR REMOTE BONDLINE THICKNESS MEASUREMENT

CROSS-REFERENCE TO RELATED APPLICATIONS

The contents of U.S. Pat. No. 6,722,202 to Kennedy; application Ser. No. 10/752,890, entitled "Non-Destructive Inspection Device for Inspection Limited-Access Features of a Structure," filed Jan. 7, 2004; application Ser. No. 10/943,088, entitled "Magnetically Attracted Inspecting Apparatus and Method Using a Ball Bearing," filed Sep. 16, 2004; application Ser. No. 10/943,135, entitled "Magnetically Attracted Inspecting Apparatus and Method Using a Fluid Bearing," filed Sep. 16, 2004; and application Ser. No. 10/943,170, entitled "Alignment Compensator for Magnetically Attracted Inspecting Apparatus and Method," filed Sep. 16, 2004, are incorporated herein by reference in their entireties.

FIELD OF THE INVENTION

The present invention relates generally to an apparatus and method for inspecting a structure and, more particularly, to an apparatus, system, and method for measuring remote bondline thickness using a pair of magnetically coupled inspection probes.

BACKGROUND

Manufacturing and assembly of composite materials often now involves assembling structures using bonded joints, such as room temperature adhesive paste bonded joints, instead of traditional fasteners. In addition to inspecting the bondline for potential damage or flaws, such as voids or cracks, verifying bondline thickness can be crucial to ensuring proper strength of the bonded joint. For example, if the bondline is too thick, the joint can be weakened. Accordingly, it is useful to be able to verify the thickness of bondlines, including remotely located bondlines which may not be easily accessed for measurement, either continuously along the length of the bondline or across the area of the bonded joint or spot checks of thicknesses at particular locations. Conventionally, however, often the only way to measure bondline thickness is to remove a part to allow for measurement of the bondline or to drill a hole into the structure to permit insertion of a measurement tool and then repair the damage.

Non-destructive inspection (NDI) of structures involves thoroughly examining a structure without harming the structure or requiring significant disassembly of the structure. Non-destructive inspection is typically preferred to avoid the schedule, labor, and costs associated with removal of a part for inspection, as well as avoidance of the potential for damaging the structure, such as drilling a hole into a structure for insertion of a measurement tool. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing of a structure and/or once a structure is in-service. For example, inspection may be required to validate the integrity and fitness of a structure during manufacturing and ongoing and future use while in-service, including verifying the thickness of a bondline. However, access to interior surfaces and bondlines is often difficult or impossible without disassembly or damage to the structure, such as removing a part or drilling a hole into a structure for insertion of a measurement tool.

Among the structures that are routinely non-destructively tested are composite structures, such as composite sandwich structures and other adhesively bonded panels and assemblies, many with interior bonded joints, such as on the interior walls of an aircraft. In this regard, composite structures, such as composite stiffeners and sandwich (honeycomb) fuselages, are commonly used throughout the aircraft industry because of the engineering qualities, design flexibility and low weight of composite structures, such as the stiffness-to-weight ratio of a composite sandwich structure. As such, it is frequently desirable to inspect composite structures to identify any flaws, such as cracks, voids or porosity, which could adversely affect the performance of the composite structure and, as previously mentioned, thicknesses of bondlines which could weaken structures and the overall product. However, as mentioned above, many bonded joints are located on the interior of a product where the bondline may be inaccessible for inspection.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bondlines of the structure, and measurement of bondline thickness. For example, conventional measurement of bondline thickness using pulse echo ultrasonic inspection may involve an ultrasonic test system with a pulser/receiver card for sending an electronic impulse signal to a pulse echo ultrasonic transducer, which translates the electronic impulse signal into an ultrasonic pulse. The ultrasonic pulse (or stress wave) travels through the structure (or part) under inspection and is partially reflected at the near and far sides of the bondline. The reflections return to the pulse echo ultrasonic transducer, which translates the reflected pulses back into electronic signals, which are communicated back to the pulser/receiver card for further analysis by the pulser/receiver car or a processing element of the ultrasonic test system and/or presentation by the ultrasonic test system. Typically, the reflected pulses are shown on a display screen, graphically and/or in some form to provide data regarding the time differential between the reflected pulses. The difference in time between the two reflections from the near and far sides of the bondline is used to calculate the thickness of the part. Half the time difference between the near- and far-side reflections multiplied by the wave speed in the bond material is equal to the thickness of the bondline, as provided by the following equation.

$$\frac{\Delta t \times \text{wavespeed in adhesive bond material}}{2} = \text{bondline thickness} \qquad \text{Eq. 1}$$

Halving the time difference multiplied by the wave speed accounts for the stress wave twice passing through the thickness of the bond material, first when traveling through the bond material to the far side of the bondline and second when reflecting from the far side of the bondline back toward the pulse echo ultrasonic transducer. Software of an ultrasonic test system may command a processing element, such as a computer processor, to automatically calculate the bondline thickness from the time differential of the reflections and a known wave speed through the bond material. A known wave speed through the bond material may be determined, and the system calibrated, using a calibration block with various bondline thicknesses of the bond material.

Non-destructive ultrasonic testing often involves coupling an ultrasonic signal from a transducer or transducer array to the surface of the structure under inspection, such as bubbling water between an inspection device and the structure. While solid laminates may be inspected using one-sided pulse echo ultrasonic (PEU) testing and bondline thickness may be measured using one-sided pulse echo ultrasonic testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as PEU and TTU transducers, is typically processed by a processing element, and the processed data may be presented to a user via a display.

Non-destructive inspection may be performed manually by technicians who move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. Similarly, non-destructive bondline thickness measurement inspection often requires a technician to locate and map the position of a bondline and then inspect the bondline, such as by passing a pulse echo ultrasonic transducer device along the bondline. The quality of the inspection, therefore, depends in large part upon the technician's performance, not only regarding the motion of the sensor, but also the attentiveness of the technician in interpreting the displayed data. More particularly, a technician's ability to perform inspection often is limited by the access the technician has to a location for placing a pulse echo ultrasonic sensor, such as at a remotely located internal surface position. For example, pulse echo ultrasonic measurement of a bondline on a composite sandwich structure is only possible from the bonded side of the structure because the core, often honeycomb, structure is a barrier to pulse echo stress waves.

Accessibility to the structure and, particularly for bondlines, accessibility to a particular side of a structure for inspection are considerations in choosing a non-destructive inspection device a limitation to being able to perform certain non-destructive inspection activities, such as measuring a remote bondline thickness. For example, access to a remote bondline (a bondline located in a remote position) may be so limited or inaccessible that a manual inspection by a technician is not possible or would require damage to the structure. Alignment and positioning of sensors such as, pulse echo ultrasonic transducers and devices therefor, is similarly complicated by accessibility to the structure such as inaccessibility to one side of a composite sandwich structure.

Accordingly, a need exists for an improved non-destructive inspection device and method to inspect a structure, particularly for measurement of remote bondline thickness.

SUMMARY OF THE INVENTION

Improved apparatus, systems, and methods for inspecting a structure, such as a composite sandwich structure and particularly for measuring a remote bondline thickness, are provided which use magnetically coupled probes to locate, position, and support an ultrasonic transducer for non-destructive inspection. The present invention allows a technician to locate, move, and accurately position, a pulse echo ultrasonic sensor for measuring a remote bondline thickness.

An inspection apparatus, system, or method according to an embodiment of the present invention advantageously may provide increased access to surfaces of a structure for inspection, such as providing access to remote bondlines for thickness measurements. An apparatus according to the present invention provides a probe including a pulse echo ultrasonic sensor and a placement rod. A method or system of the present invention uses a pair of magnetically coupled probes, a tracking probe having a pulse echo ultrasonic sensor and a magnetically coupled driven probe, disposed proximate opposite surfaces of a structure. The magnetic coupling between the probes may be used for moving, positioning, and maintaining alignment of the pulse echo ultrasonic sensor of the tracking probe for inspection. Thus, apparatus, systems, and methods of the present invention are advantageously adapted to inspect structures in which one surface of the structure is relatively inaccessible, such as a remotely located bondline.

A system of one embodiment of the present invention includes a driven (or control) probe disposed proximate a first surface of the structure and a tracking (or follower) probe disposed proximate an opposed second surface of the structure. The driven probe is moved along the first surface of the structure in response to the application of motive force, such as by a technician positioning the driven probe on the opposite surface of a structure from a bondline. In contrast, the tracking probe generally moves along the second surface of the structure in response to the movement of the driven probe and independent of the application of any other motive force. Thus, the tracking probe generally passively follows the movement of the driven probe in a leader-follower operation. Therefore, the tracking probe can be disposed on the backside or other surface of a structure that is relatively inaccessible, such as a remotely located bondline.

To facilitate the coordinated movement of the tracking probe in conjunction with the driven probe, both the driven probe and the tracking probe advantageously include one or more magnets which draw the driven and tracking probes toward the first and second surfaces of the structure, respectively. Ring magnets may be used in the driven and tracking probes to provide magnetic coupling of the two probes to the respective surfaces of the structure. Additionally, the magnetic attraction between the magnets of the driven and tracking probes causes the tracking probe to be moved over the second surface of the structure in response to corresponding movement of the driven probe.

The tracking probe includes a pulse echo ultrasonic sensor, typically a pulse echo ultrasonic transducer and standoff, for measuring bondline thickness. For a tracking probe having a ring magnet, a pulse echo ultrasonic sensor may be positioned at the center of the ring magnet; thus, as the ring magnets of the probes align the two probes on respective surfaces of the structure, the pulse echo ultrasonic sensor of the tracking probe is also aligned at the centers of the ring magnets.

To facilitate the coupling of the ultrasonic signal between the pulse echo ultrasonic sensor of the tracking probe and the structure, a couplant may be disposed between the sensor and the respective surface of the structure. A tracking probe of one advantageous embodiment includes fluid ports for pumping a fluid, typically water, into channels for evenly distributing the fluid between the sensor and the structure. In this regard, the tracking probe may include a housing in which the magnet and the pulse echo ultrasonic sensor are disposed. The channels may be, for example, a series of radially directed recesses or a plurality of holes. Where the channels include radially directed recesses, the channels may also include a ring shaped recess for evenly distributing fluid around the radially directed recesses.

According to one aspect of the present invention, an apparatus for inspecting a structure to measure bondline thickness is provided. The apparatus provides a tracking probe including a pulse echo ultrasonic sensor and a placement rod. The placement rod is used for placing and/or removing the tracking probe from a remote position about a structure under inspection. A placement rod may be connected to the tracking probe in a variety of manners, including, without limitation, a magnetically connection and a flexible attachment such as a lanyard.

According to another aspect of the present invention, a method of inspecting a structure to measure bondline thickness is provided. In this regard, the tracking probe is positioned proximate a second surface of the structure, and the driven probe is positioned proximate an opposed first surface of the structure. Magnetic attraction is established between the driven and tracking probes such that the driven and tracking probes are drawn toward and hold to the first and second surfaces of the structure, respectively. The driven probe is moved along the first surface of the structure to position a pulse echo ultrasonic sensor of the tracking probe. The movement of the driven probe and the magnetic attraction between the driven and tracking probes causes the tracking probe, and pulse echo ultrasonic sensor thereof, to be correspondingly moved along the second surface of the structure. Advantageously, the tracking probe moves along the second surface of the structure independent of the application of any motive force. Thus, the tracking probe may be disposed proximate a relatively inaccessible surface of a structure since the movement of the tracking probe need not be controlled independently from the driven probe. Pulse echo ultrasonic inspection signals are transmitted from the pulse echo ultrasonic sensor into the structure and reflected inspection signals are received from the structure which are reflected from the near and far sides of a bondline of the structure. To effectively couple the ultrasonic inspection signals between the pulse echo ultrasonic sensor and the structure, a fluid may be pumped between the sensor and the second surface of the structure.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

DETAILED DESCRIPTION

The present invention will be described more fully with reference to the accompanying drawings. Some, but not all, embodiments of the invention are shown. The invention may be embodied in many different forms and should not be construed as limited to the embodiments described. Like numbers and variables refer to like elements and parameters throughout the drawings.

Figure 1:
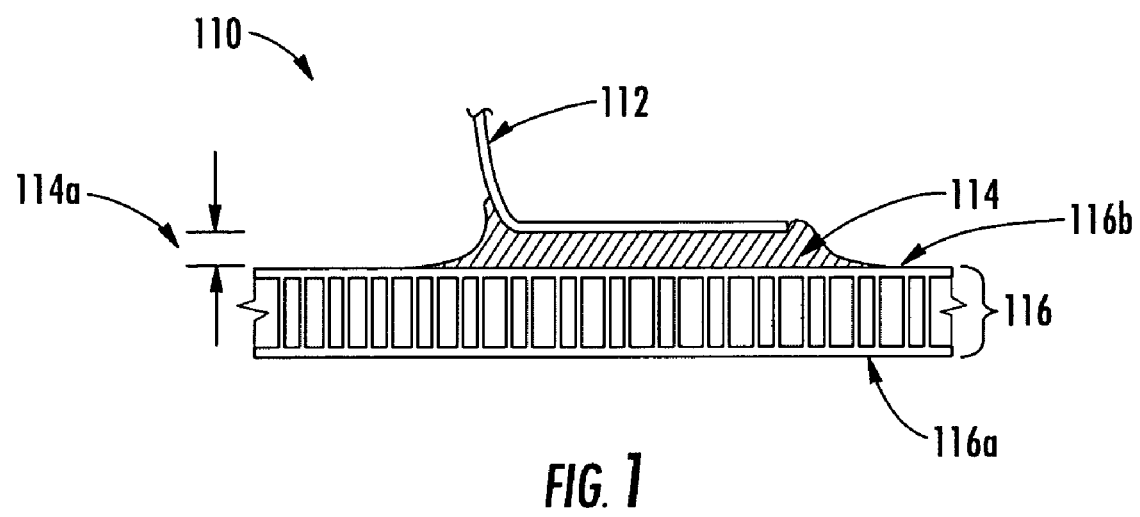
FIG. 1 is a schematic diagram of a composite sandwich structure with an adhesive paste bond joint to a second composite structure.

FIG. 1 is a schematic diagram of a composite sandwich structure 116 with an adhesive paste bond joint to a second composite structure 112, such as a bonded stiffener the thickness of which can be measured in accordance with the present invention. The composite sandwich structure 116 includes a honeycomb core layer which prevents measurement of the thickness of the bondline 114a using a pulse echo ultrasonic inspection method from the exterior side 116a of the composite sandwich structure. Rather, the thickness of the bondline 114a may be measured using pulse echo ultrasonic inspection from the unbonded side 112a of the adhesively bonded second composite structure attachment 112, also generally referred to as measuring the bondlines thickness from the bonded side 116b of the structure 116. The bondline thickness 114a is representative of the thickness of the amount of adhesive bond material 114 between the adhesively bonded second composite attachment 112 and the bonded surface 116b of the composite sandwich structure 116. This adhesive paste bond joint configuration 110 forms a bondline along the length of the joint, but may also be representative of a joint area when a larger bond may be used to attach to members. Thicknesses of similar other configurations of adhesive paste bondlines may also be measured in accordance with the present invention.

Referring now to FIGS. 2, 3, 4, and 5, apparatus 14, 16 for inspecting a structure to measure bondline thickness according to one embodiment of the present invention are depicted. The apparatus can inspect a variety of structures formed of various materials. Since the apparatus rely to some extent upon the establishment of magnetic fields through the structure, however, the structure is preferably non-magnetic. Structures that may be inspected with an embodiment of the present invention may include, but are not limited to, composites, non-ferromagnetic metals (e.g. aluminum alloy, titanium alloy, or aluminum or titanium hybrid laminates such as GLARE or Ti/Gr), and polymers. It should be noted that the surfaces, and the material therebetween such as intermediate surfaces commonly referred to as septums, which collectively define the material through which the driven and tracking probes are magnetically coupled, preferably comprise a non-ferromagnetic material because the magnetic coupling between the probes would be diminished or eliminated by a ferromagnetic material located between magnetically coupled inspection probes in accordance with the present invention.

Figure 2:
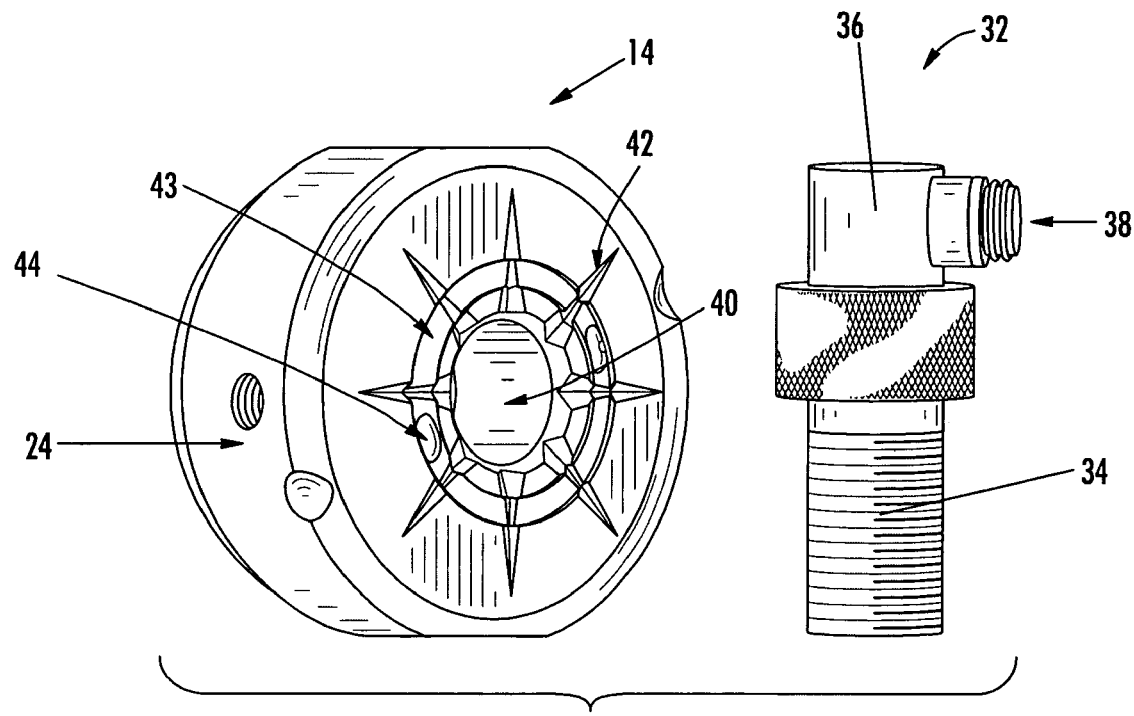
FIG. 2 is a schematic diagram of a probe viewed from the surface-side of the probe and a pulse echo ultrasonic transducer and standoff sensor according to an embodiment of the present invention.
Figure 3:
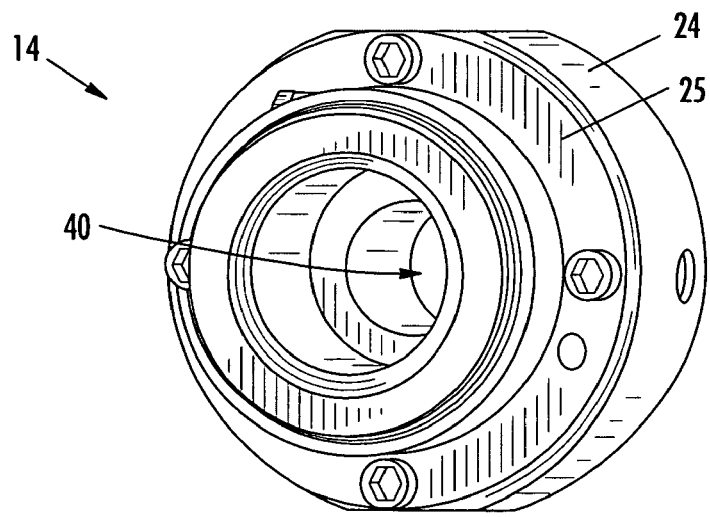
FIG. 3 is a schematic diagram of another view of the probe of FIG. 2.
Figure 4:
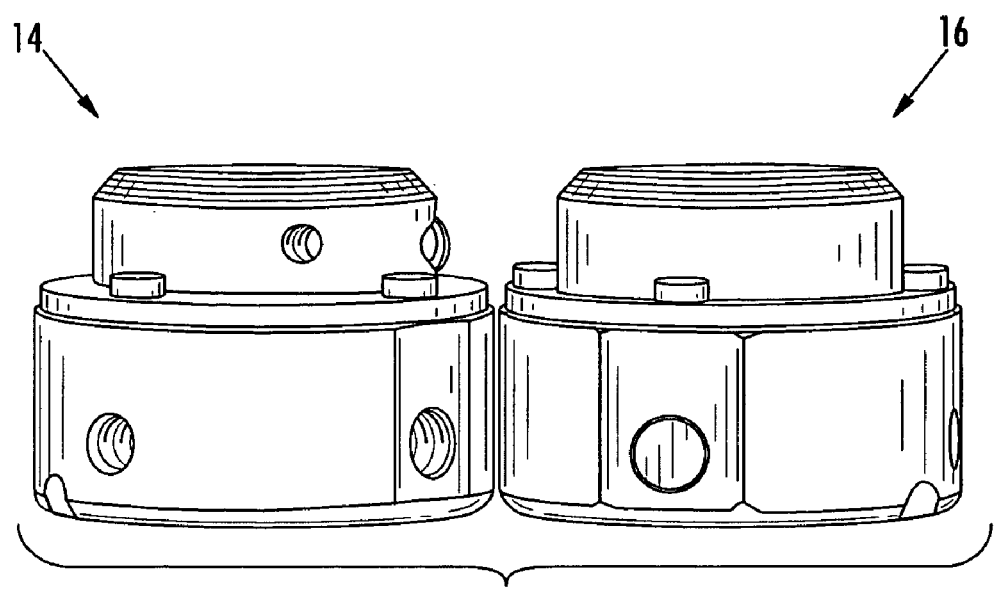
FIG. 4 is a schematic diagram of a pair of probes according to an embodiment of the present invention.
Figure 5:
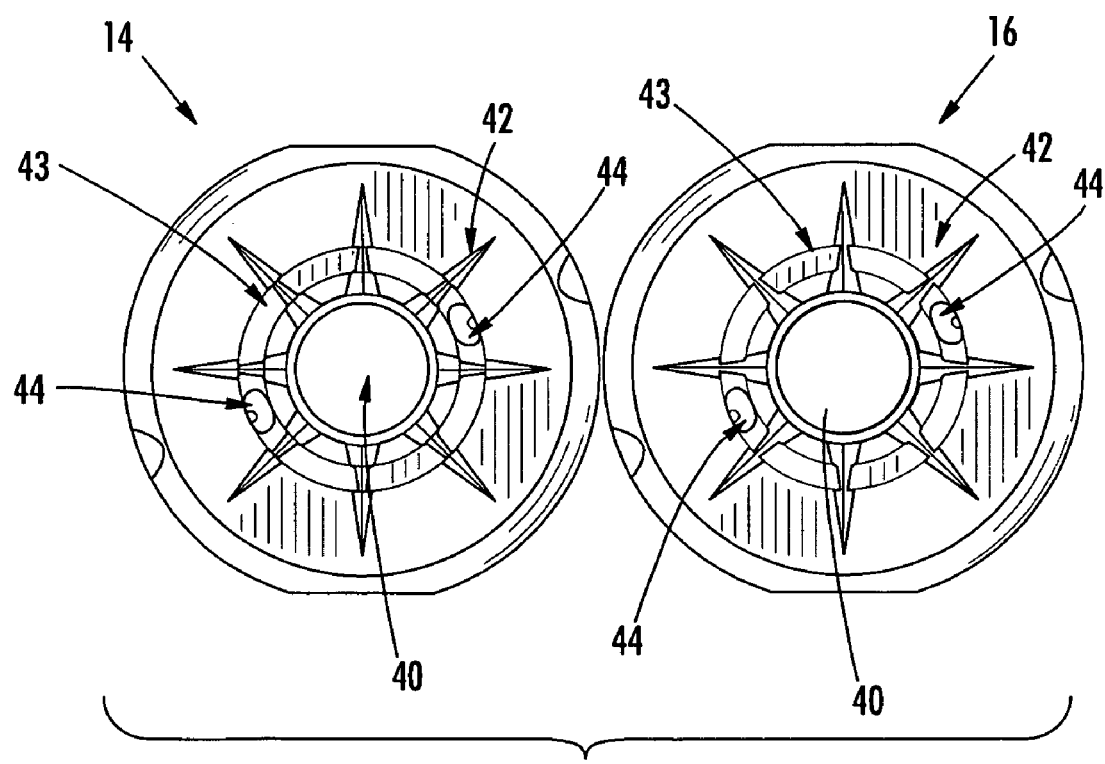
FIG. 5 is a schematic diagram of a surface-side view of the pair of probes of FIG. 4.

FIGS. 2 and 3 are schematic diagrams of a probe according to the embodiment of the present invention. FIG. 2 is a view of the probe from the surface-side (bottom) of the probe, i.e., the side of the probe which rests against the surface of the structure during inspection operations, and a pulse echo ultrasonic sensor with a transducer and standoff. FIG. 3 is a schematic diagram of the probe as viewed toward the surface of a structure against which the probe may be positioned. FIGS. 4 and 5 are schematic diagrams of a pair of probes according to an embodiment of the present invention. The present invention operates using a pair of probes 14, 16, although the structure of the probes may be identical with possible exceptions of, for example, whether or not a probe includes a pulse echo ultrasonic sensor 32 or an alignment compensator attachment, as described further below. The driven probe 16 may be referred to as the control probe or control shoe, and the tracking probe 14 may be referred to as the inspection probe or follower probe where the driven and tracking probes 16, 14 operate in a leader-follower configuration. Each probe 14, 16 includes a magnet typically disposed within a housing 24. The magnets of the probes magnetically attract the driven and tracking probes 16, 14 toward respective surfaces of a structure under inspection. Magnets of the illustrated embodiments likely are ring magnets. Using probes with ring magnets on opposing surfaces of a structure also aids in aligning the two probes with respect to the other. By comparison, magnetically coupled inspecting probes using bar magnets, flat magnets, cylindrical magnets, and the like, may require configurations of magnets and/or ferromagnetic materials to align the probes. Such configurations typically cannot provide the flexibility of ring magnets which may permit a tracking probe to rotate freely with respect to a magnetically coupled driven probe while maintaining alignment of a pulse echo ultrasonic sensor 32 located within the center of a ring magnet in the tracking probe 14. Magnetically coupled probes employing embodiments of the present invention may alternatively, or in addition, use magnets and/or ferromagnetic materials to provide alignment and/or magnetic attraction between probes. While each probe may include any number of magnets, each probe need only include one ring magnet which reduces the size, weight, cost, and complexity of the probes. Magnets of the illustrated embodiments may be ring magnets formed of neodymium iron boron, which advantageously have greater magnetic flux (around 12,000 gauss) than standard ceramic or ferrite magnets (around 3,900 gauss). Further embodiments of the invention may include magnets of different material, such as Samarium Cobalt or Alnico and/or electromagnets or other magnetic coupling means. The term "magnet" as used herein is inclusive of electromagnets. The probes of the present invention may further comprise magnetic shunting mechanisms to control the magnetic flux of the magnetic couplings, a non-limiting example being rare earth metal switched magnetic devices disclosed in U.S. Pat. No. 6,180,928. While various types of ring magnets may be used, the driven and tracking probes of one embodiment include permanent ring magnets, such as NdFeB ring magnets. The size of ring magnets for both the driven and tracking probes may be dependent, at least in part, upon the weight of the respective probes, the thickness of the structure undergoing inspection, and the material that forms the structure undergoing inspection. Additionally, driven and tracking probes may include ring magnets having either the same or different sizes. Different size ring magnets may help to maintain alignment of the probes and may permit adjustment of the weight of a probe, such as to reduce the weight of a probe which hangs beneath the surface of a structure.

The housing 24 may be preferably constructed of various non-magnetic materials and, in one embodiment, is constructed of Delrin® material available from E.I. DuPont Nemours and Company of Wilmington, Del. The magnets may be ring magnets to accommodate a circular design which provides for locating the pulse echo ultrasonic sensor 32 within the centers 40 of the ring magnet and of the housing 24 of the tracking probe 14. A cap 25 may be attached to the housing 24 to secure the magnet within a recess defined in the housing 24. However, a particular shape or configuration of a magnet or housing is not required for the present invention. Similarly, the shape and size of an inspection probe which may employ the present invention is not limited to the specific embodiments described and disclosed herein, but may be any shape or size capable of operating in accordance with the present invention. For example, the driven and tracking probes 16, 14 of the present invention may be scaled-down and simplified versions of larger inspection probes described in U.S. patent application Ser. Nos. 10/943,088 and 10/943,135, which also describe example embodiments for configuration of inspection probes which may be used or adapted for use according to the present invention. And, as described, and unlike through transmission ultrasonic inspection which requires a pair of transmitting and receiving ultrasonic sensors, the present invention requires only a single pulse echo ultrasonic sensor 32 as part of a tracking probe 14.

The surface-side of a housing 24 may include channels 42, 43 to direct a flow of fluid to assist movement of a probe, such as to create a fluid bearing, and/or to provide fluid coupling between a pulse echo ultrasonic sensor 32 and a surface of a structure. Typically, however, fluid is only used as a couplant for the present invention, and fluid flow need only be great enough to provide a mere bubbling of fluid. The channels on the surface-side of a housing may be recesses 42, holes, or other indentations and/or outlets for a fluid. As shown in FIGS. 2 and 5, a radial, star-like pattern of recesses 42 may be defined by the surface-side of the housing 24. A star pattern provides an even distribution and flow of fluid over the face of the probe. A circular recess 43 in the surface-side of the housing 24 provides for even distribution and flow of a fluid around the radial pattern of recesses 42 for even distribution and flow of the fluid over the face of the probe. Fluid ports 44 located in the circular ring recess 43 provide for introduction of the fluid from the housing 24 into the circular recess 43 for even distribution around the radial pattern of recesses 42. If the fluid is used for a couplant between a pulse echo ultrasonic sensor 32, the channels 42, 43, such as the radial pattern of recesses 42, may be designed to provide for a flow of fluid between the pulse echo ultrasonic sensor 32, particularly a standoff 34 thereof, and a surface of a structure against which the tracking probe 14 is positioned. Advantageously, the channels 42, 43 are designed to permit a fluid to flow smoothly over and between the pulse echo ultrasonic sensor 36, particularly a standoff 34 thereof, and a surface of a structure under inspection without bubbles, cavitation, or turbulence that could otherwise detrimentally affect the signal to noise ratio of the ultrasonic inspection. Alternatively, an ultrasonic gel may be used as a couplant rather than bubbling a fluid between a standoff 34 and a structure.

The pulse echo sensor 32 includes a pulse echo ultrasonic transducer 36 and a standoff 34. A connection point 38 may be attached to the pulse echo ultrasonic sensor 32 for connecting the pulse echo ultrasonic transducer 36 with an ultrasonic test system, such as to communicate reflected inspection signals to a processing element of the ultrasonic test system. The face of the pulse echo ultrasonic transducer 36 touches one end of the standoff 34, often with an ultrasonic couplant between the transducer 36 and the standoff 34 to ensure that ultrasonic stress waves effectively travel down into the standoff 34 from the transducer 36. A standoff is typically used with pulse echo ultrasonic inspection as a medium for an ultrasonic stress wave to travel from the pulse echo ultrasonic transducer to and into the structure under inspection. Use of a standoff prevents the reflection from the first surface of the structure under inspection from interfering with the signal returning from inside the structure. Often, a standoff is made from acrylic or from Plexiglas™ of the Rohm & Haas Company of Philadelphia, Pa.

Figure 6:
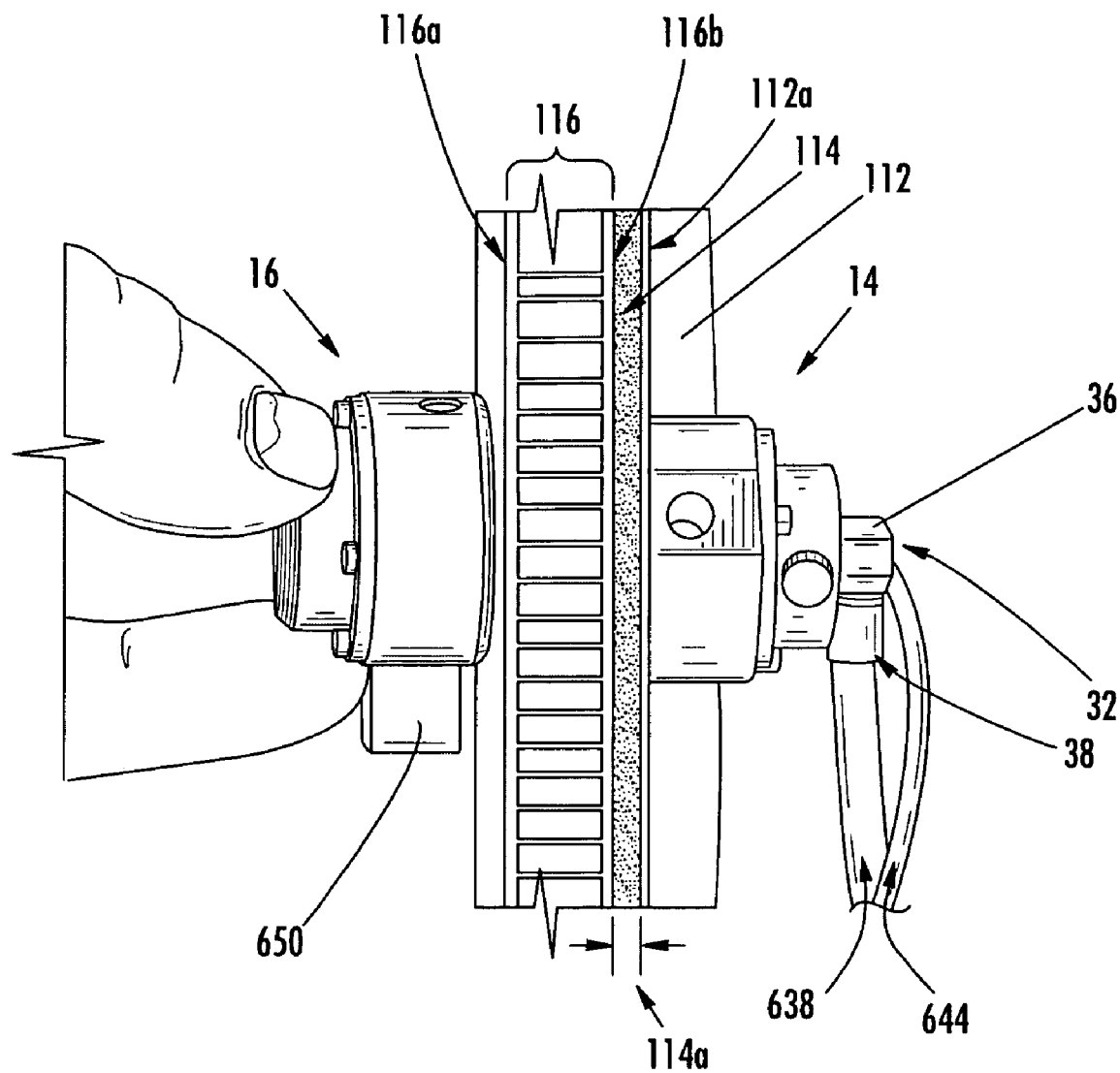
FIG. 6 is a schematic diagram of remote bondline measurement using a pair of probes according to an embodiment of the present invention.

FIG. 6 is representative of an embodiment of a system of the present invention and includes a driven probe 16 disposed proximate a first surface 116a of the structure 116 and a tracking probe 14 disposed proximate an opposed second surface 116b of the structure 116 having a bonded joint thickness 114a separating the core structure 116 from an adhesively bonded structure 112. In effect, inspection of the core structure 116 to measure a bondline thickness 114a refers to measuring the thickness 114a of the bond material 114 between the core structure 116 and the bonded structure 112, and is generally referred to herein as inspecting the structure 116 to measure a bondline thickness 114a of the structure 116. This distinction is also described and depicted with reference to FIG. 1. The bonded structure 112 is generally considered and referred to as part of the overall structure referenced by the core structure 116, and a tracking probe 14 riding on the second surface 116b of the structure 116 technically refers to the tracking probe 14 riding on the exposed, non-bonded surface 112a of the bonded structure 112. However, not all bondlines will possess the configuration depicted in FIG. 6, so a more general description is used whereby the driven and tracking probes 16, 14 are magnetically coupled across the core structure 116 and are used to measure a bondline thickness 114a thereof.

Figure 7:
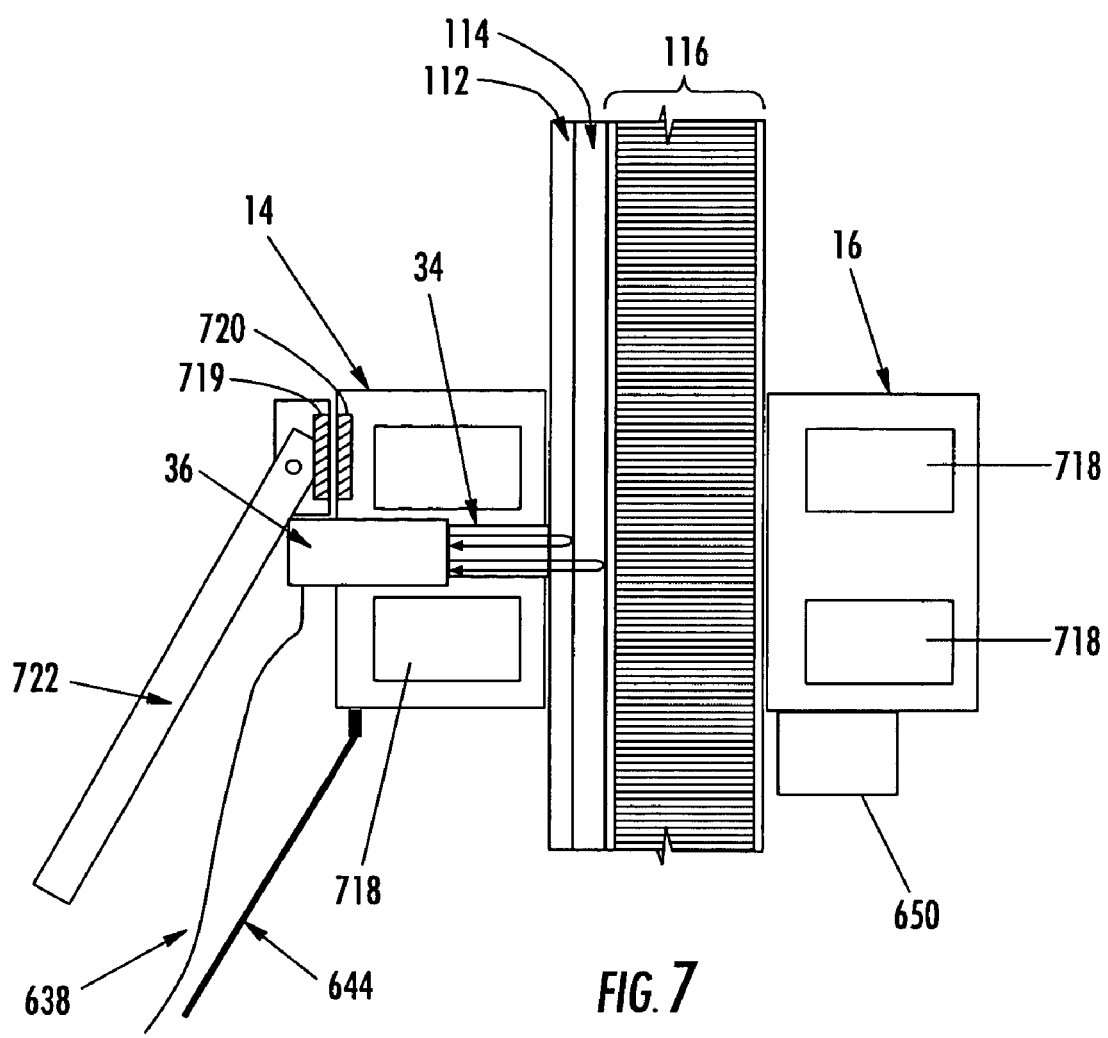
FIG. 7 is a schematic diagram of remote bondline measurement using a pair of probes according to an embodiment of the present invention.
Figure 8A:
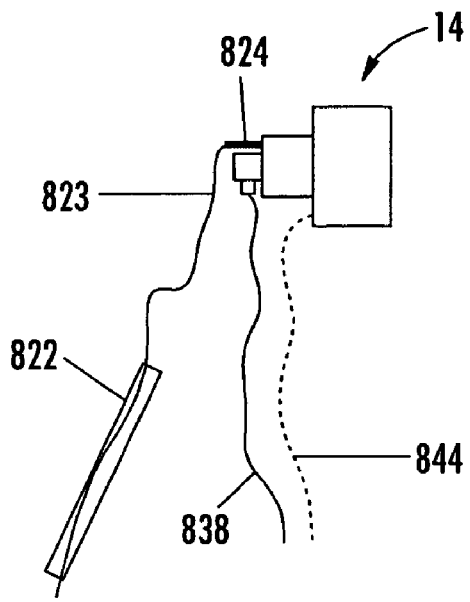
FIG. 8A is a schematic diagram of a probe according to an embodiment of the present invention.
Figure 8B:
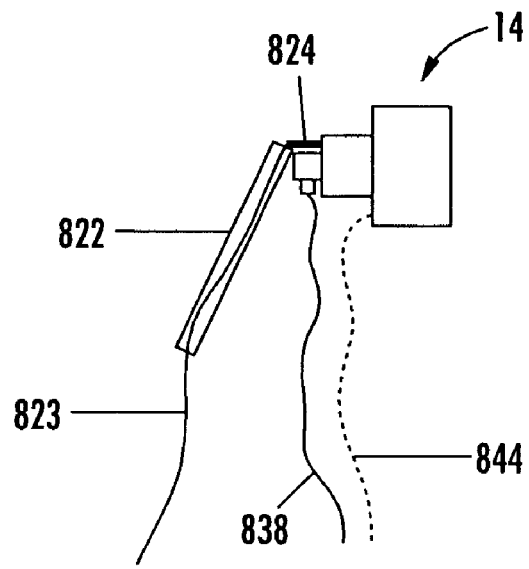
FIG. 8B is another schematic diagram of the probe of FIG. 8A.
Figure 9A:
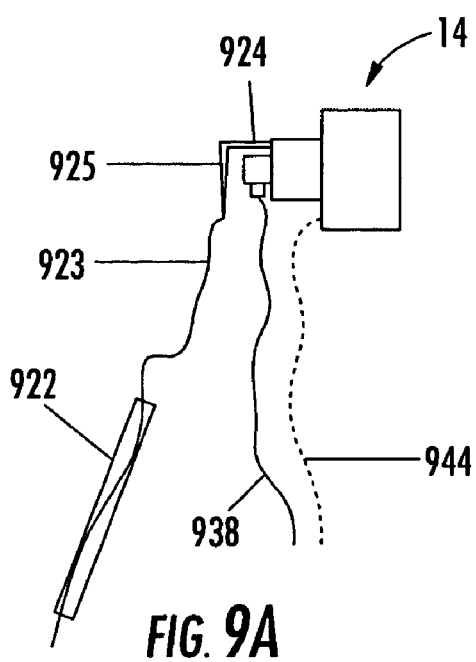
FIG. 9A is a schematic diagram of a probe according to an embodiment of the present invention.
Figure 9B:
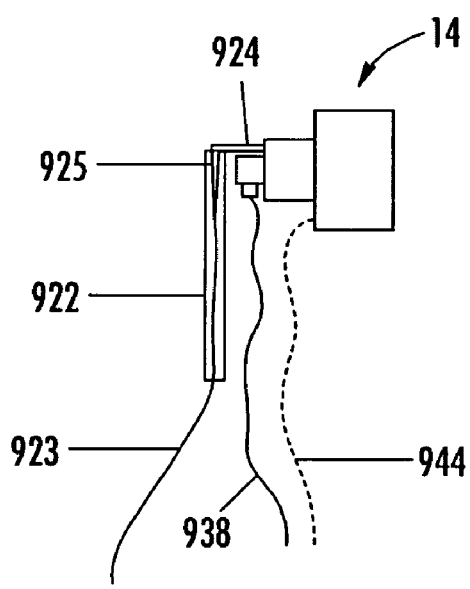
FIG. 9B is another schematic diagram of the probe of FIG. 9A.

The driven and tracking probes 16, 14 may be disposed in contact with first and second surfaces 116a, 116b (112a) of the structure 116, and are advantageously initially positioned in alignment so as to be directly opposed one another or otherwise in positional correspondence with one another, as shown in FIGS. 6 and 7. This alignment allows the probes 14, 16 to establish magnetic attraction to magnetically couple the probes 14, 16 and provides a positional relationship between the probes 14, 16 such that one probe is not translated or offset vertically (or laterally) across a surface of the structure 116 from the other probe. As described below, this positional relationship or correspondence between the driven and tracking probes is maintained as the probes are moved along respective surfaces of the structure. As a result of the magnetic attraction established between the driven and tracking probes 16, 14 and, more particularly, between magnets of the driven and tracking probes 16, 14, the tracking probe 14 moves in a like manner and in correspondence with the driven probe 16 without requiring the application of any additional motive force directly to the tracking probe 14. Thus, the tracking probe 14 moves so as to remain in an aligned, opposed position relative to the driven probe 16 as the driven probe 16 is moved along a first surface 116a of a structure 116. As such, the tracking probe 14 need not be independently moved, except for initial placement, removal, and, possibly, for intermediate relocation. Accordingly, the tracking probe 14 can be disposed proximate to and can ride along a portion of a second surface 116b of a structure 116 that is relatively inaccessible.

Although ring magnets may be used independently to positionally align probes of embodiments of the present invention, as described with reference to FIGS. 2, 3, 4, and 5, rotational alignment of probes may be enhanced by incorporating at least one additional magnet or ferromagnetic material to at least one of the probes. Selecting the magnetic polarity of at least one additional magnet of one of the probes to be such that the respective additional magnet is repelled by one or more of the magnets of the other probe or attracted by one or more of the magnets or a ferromagnetic material of the other probe. For example, if one of the probes includes ferromagnetic material, such as a plug of ferromagnetic material, the other probe may include an additional magnet positioned such that the probes are properly positioned with respect to one another when the ferromagnetic plug and the additional magnet are aligned since the ferromagnetic plug and the additional magnet of the other probe will be attracted to one another when these elements are properly aligned to position the probes with rotational alignment. Similarly, if the probes each include two additional magnets, where the two additional magnets of each probe have opposite polarities, when the probes are misaligned, the additional magnets of the probes would be repelled and produce a rotation of the probes until the additional magnets of the probes align with the additional magnets of the other probe that are of the opposite polarity. As such, these types of additional magnets and ferromagnetic materials may be used as rotational alignment keys for an apparatus of an embodiment of the present invention. Further, to accommodate for misalignments such as due to the pull of gravity, an alignment compensator 650, as described in U.S. patent application Ser. No. 10/943,170, may be added to one of the probes, such as attached to the driven probe 16 in FIG. 6.

The tracking probe 16 includes a pulse echo ultrasonic sensor 32 for inspecting the structure 116 to measure bondline thickness 114a. A data and power cable 638 may be connected at a connection point 38 to the pulse echo ultrasonic sensor 32 for such data and power transmissions between the pulse echo ultrasonic transducer 36 and a pulser/receiver board or like device as signals instructing the pulse echo ultrasonic sensor 32 to transmit an ultrasonic inspection signal from a pulse echo ultrasonic transducer 36 for measuring bondline thickness and data representing a reflected ultrasonic inspection signal. A fluid supply line 644 may be connected to an inspection probe, such as connected to the tracking probe 16 in FIG. 6, to supply fluid which may be used as a couplant between a pulse echo ultrasonic sensor 32, particularly a standoff thereof, and a surface of a structure under inspection and/or used to assist movement of a probe over a surface, such as to lubricate the surface or to create a fluid bearing.

Such inspection probes provide for coordinated movement using magnetic coupling between the driven and tracking probes to permit positioning and control by the driven probe 14 of the tracking probe 16 which performs pulse echo ultrasonic inspection for bondline measurement. As known for pulse echo ultrasonic non-destructive inspection for measuring bondline thickness, the ultrasonic pulse (or stress wave) travels from the pulse echo ultrasonic sensor, typically from a pulse echo ultrasonic transducer down through a standoff to the structure, through the structure (or part) under inspection, specifically to and through a bonded joint material, and is partially reflected at the near and far sides of the bondline. The reflections return to the pulse echo ultrasonic transducer, which translates the reflected pulses back into electronic signals, which are communicated back to a pulser/receiver card for further analysis and/or presentation by the ultrasonic test system. The difference in time between the two reflections from the near and far sides of the bondline are used to calculate the thickness of the part. Half the time difference multiplied by the wave speed in the bond material is equal to the thickness of the bondline, as provided by the following equation.

$$\frac{\Delta t \times \text{wavespeed in adhesive bond material}}{2} = \text{bondline thickness} \quad \text{Eq. 1}$$

Half the time difference multiplied by the wave speed accounts for the stress wave twice passing through the thickness of the bond material, first when traveling through the adhesive bond material to the far side of the bondline and second when reflecting from the far side of the bondline back toward the pulse echo ultrasonic transducer.

While a portion of a composite structure 116 with a bonded attachment 112 is depicted during the course of an inspection in FIGS. 6 and 7, a structure inspected by an embodiment according to the present invention may be any myriad of shapes and/or sizes. In addition, the structure that is inspected may be used in a wide variety of applications, including in vehicular applications, such as in conjunction with aircraft, marine vehicles, automobiles, space craft and the like, as well as other non-vehicular applications, such as in conjunction with buildings and other construction projects. Moreover, the structure may be inspected during manufacturing, prior to assembly, following assembly, or in-service as desired.

FIG. 7 is a schematic diagram of remote bondline measurement operation according to an embodiment of the present invention. Unlike the schematic diagram of FIG. 6, the schematic diagram of FIG. 7 shows a cross-section of embodiments of driven and tracking probes 16, 14 magnetically coupled on opposite sides of the structure 116. Further, a placement rod 722 is detachably connected to the tracking probe 14 for initially placing the tracking probe 14 in a remote access location, such as in a difficult to reach interior location. In operation, a technician will first position the tracking probe 14 proximate a surface of the structure under inspection and, preferably over the bondline for which a thickness measurement will be taken. Contemporaneously, either before, after, or at approximately the same time, a driven probe 16 is positioned proximate the opposing surface of the structure to establish magnetic attraction between the two probes 14, 16 to hold the probes against the structure and to provide magnetic coupling for moving and positioning the tracking probe 14 by coordinated movement of the driven probe 16. To assist a technician in initially placing a tracking probe 14, a placement rod 722 may be used. A placement rod 722 generally is an extension of the technician's arm, typically providing additional length for accessing an out-of-reach, remote location and/or providing a formable extension for reaching into an otherwise inaccessible location, such as when another structure is in the way. A placement rod 722 may be rigid (or stiff) or deformable (or formable). If rigid, the placement rod 722 may still include a bend (or elbow) for reaching around corners or structures. Various methods and/or materials may be used to provide a deformable placement rod, such as to use a bendable metal or to use one or more adjustable hinges along the length of the placement rod. A typical placement rod may be formed from two ridged segments (lengths) connected by a ratcheted hinge to provide an adjustable bend angle. One or more rigid segments of a placement rod may also be telescoping members to permit adjustment of the length of those rigid segments. In such a manner, and in combination with one or more bendable segments and hinges, a placement rod may be formed into a placement rod of generally any shape and size.

A placement rod 722 typically also is connected to a tracking probe 14 by a detachable connection, such as using a magnetic connection or a releasable attachment. For example, the connection between the placement rod 722 and the tracking probe 14 need merely be fixed for as long as the technician is placing the tracking probe 14. Once the tracking probe is in position, and magnetically coupled to a driven probe 16, the placement rod 722 typically will no longer be required, and preferably may be detached to permit movement and positioning of the tracking probe 14 by the driven probe 16. Accordingly, a placement rod 722 may be connected, for example, as in FIG. 7, using magnetic coupling elements 719, 720 at the end of the placement rod 722 and on the tracking probe 14. The magnetic attraction between these magnetic coupling elements 719, 720 may be strong enough to support the tracking probe 14 on the placement rod 722 for initial placement by a technician, but weak enough to decouple when the tracking probe 14 is magnetically coupled to a driven probe 16, thereby permitting the placement rod 722 to be detached and moved free of the tracking probe 14. Other detachable connections, such as a mechanically or electrically releasable latch, may be used between a placement rod 722 and a tracking probe 14.

FIGS. 8A, 8B, 9A, and 9B show how a lanyard may be connected to a probe for providing a secure connection to the probe for when a placement rod has been detached from the probe. The term "lanyard," as used herein, is inclusive of a rope, string, chain, cable, chord, thread, filament, twine, and like flexible attachment mechanisms. A lanyard, as used herein, typically will not form a loop, but may be a single length of flexible material and typically will include, but does not require, a fastener, such as a hook or clip, for releasably attaching the lanyard to a probe. A lanyard 823, 923 may be used to retrieve the tracking probe 14 when inspection is complete, similar to or by reeling in the tracking probe 14 like using a fishing pole. A lanyard may be used to pull on a tracking probe 14, rather than pulling on a data and power cable 838, 938 or a fluid supply line 844, 944, which might damage the connections for those devices. A lanyard 823, 923 may also be used to reconnect a placement rod 822, 922 to the tracking probe for retrieving the tracking probe when inspection is complete. For example, a hollow placement rod 822, 922 may slide along the length of a lanyard either to provide separation of the placement rod 822, 922 from the tracking probe 14 during inspection operations through slack of the lanyard 823, 923 or to support the tracking probe 14 for placement and/or removal. Various mechanisms may be used for cooperation of a lanyard 823, 923 and a placement rod 822, 922, including, but not limited to, a simple fixed attachment position 824 for a lanyard 823 and a hollow placement rod 822, a fixed attachment position 924 with an alignment mechanism 925 for a lanyard 923 and a hollow placement rod 922, and a detachable magnetic connection as shown in FIG. 7, although shown without a corresponding lanyard. A lanyard, or another string-like flexible attachment mechanism, may also be used for detaching a placement rod from a tracking probe, such as to release a spring-loaded latch or decouple a magnetic attachment connecting the placement rod to the tracking probe.

Many modifications and other embodiments of the inventions set forth will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed, they are used in a generic and descriptive sense only and not for purposes of limitation.

That which is claimed:

1. A system for inspecting a structure to measure bondline thickness, comprising:
    a driven probe structured for traveling over a first surface of the structure, the driven probe comprising a magnet;
    a tracking probe structured for traveling over an opposed second surface of the structure, the tracking probe comprising a magnet for cooperating with the magnet of the driven probe to draw the driven and tracking probes toward the first and second surfaces of the structure, respectively, wherein magnetic attraction between the driven and tracking probes causes the tracking probe to be moved over the second surface of the structure in response to corresponding movement of the driven probe, and wherein the tracking probe further comprises a pulse echo sensor configured for performing non-destructive inspection for measuring bondline thickness of the structure; and
    a placement rod detachably connected to the tracking probe for placement of the tracking probe in remote locations.

2. The system of claim 1, wherein the placement rod is formable to permit changing the shape of the placement rod for accommodating placement in remote locations.

3. The system of claim 1, wherein the placement rod is detachably connected to the tracking probe by magnetic coupling and permanently attached to the tracking probe by a lanyard.

4. The system of claim 1, wherein the tracking probe further comprises a fluid conduit though which fluid flows for injecting a fluid between the pulse echo sensor and the second surface of the structure.

5. The system of claim 4, wherein the fluid conduit comprises:
    a fluid inlet through which fluid enters the fluid conduit; and
    a plurality of channels through which fluid exits the fluid conduit to evenly disperse a flow of fluid over the surface of the tracking probe in proximity with the second surface of the structure.

6. The system of claim 5, wherein the channels distribute fluid between the pulse echo sensor and the second surface of the structure to provide a coupling path between the pulse echo sensor and the second surface.

7. The system of claim 1, wherein at least one of the driven and tracking probes further comprises a fluid conduit for injecting a fluid between the respective probe and the respective surface of the structure to create a fluid bearing on which the respective probe rides for moving over the respective surface.

8. The system of claim 1, wherein the pulse echo sensor comprises a pulse echo ultrasonic transducer capable of transmitting and receiving an ultrasonic signal and a standoff for translating the ultrasonic signal from the pulse echo ultrasonic transducer to the second surface of the structure through the standoff as an ultrasonic shear wave.

9. The system of claim 8, wherein the tracking probe further comprises a fluid conduit for injecting a fluid between the standoff and the second surface of the structure.

10. An apparatus for inspecting a structure to measure bondline thickness, comprising:
    a probe configured for being positioned against and moved over a surface of the structure, the probe comprising:
       a housing;
       a magnet carried by the housing; and
       a pulse echo ultrasonic sensor carried by the housing and configured for performing non-destructive inspection for measuring bondline thickness; and
    a placement rod detachably connected to the probe for initially positioning and placing the probe proximate the surface of the structure and capable of being detached from the probe.

11. The apparatus of claim 10, further comprising a lanyard connected to the probe for providing a secure connection to the probe for when the placement rod is detached from the probe.

12. The apparatus of claim 10, wherein the placement rod is detachably connected to the probe by magnetic attraction.

13. The apparatus of claim 10, wherein the placement rod formable into a plurality of configurations.

14. The apparatus of claim 10, wherein the placement rod is capable of being re-connected to the probe for removing the probe from the structure.

15. The apparatus of claim 10, wherein the housing defines:
    a fluid conduit defining an internal passage for passing fluid from a fluid inlet to at least one fluid port; and
    a plurality of channels to evenly disperse a flow of fluid from the at least one fluid port over at least a portion the surface of the housing in proximity with a surface of the structure being inspected.

16. The apparatus of claim 15, wherein the channels comprise recesses in the surface of the housing proximate to the surface of the structure being inspected wherein the recesses are directed radially from the center of the surface of the housing proximate the surface of the structure to allow fluid to flow radially through the recesses and distribute evenly between the surface of the housing proximate the surface of the structure and the surface of the structure.

17. The apparatus of claim 16, wherein the channels further distribute fluid between the sensor and the surface of the structure being inspected to provide a coupling path for the sensor of the probe.

18. The apparatus of claim 10, wherein the housing defines:
a fluid conduit defining an internal passage for passing fluid from a fluid inlet to at least one fluid port; and
a plurality of channels to evenly disperse a flow of fluid from the at least one fluid port between a portion of the sensor proximate the structure and at least a portion of the surface of the structure to provide a coupling path for ultrasonic signals from the sensor to the structure and from the structure to the sensor.

19. A method of inspecting a structure to measure bondline thickness, comprising:
placing a tracking probe proximate a second surface of the structure using a placement rod detachably connected to the tracking probe;
placing a driven probe proximate an opposed first surface of the structure;
establishing magnetic attraction between the driven probe and the tracking probe such that the driven probe and the tracking probe are drawn toward and hold the first and second surfaces of the structure, respectively;
positioning a pulse echo ultrasonic sensor of the tracking probe at a desired location on the second surface by moving the driven probe along the first surface of the structure which causes the tracking probe to be correspondingly moved along the second surface of the structure; and
transmitting inspection signals into the structure from the pulse echo ultrasonic sensor and receiving reflected inspection signals at the pulse echo ultrasonic sensor from the structure, wherein the reflected inspection signals are reflected from the near and far sides of a bondline of the structure.

20. The method of claim 19, further comprising the step of detaching the placement rod from the tracking probe after the steps of placing the tracking probe, placing the driven probe, and establishing magnetic attraction between the driven and tracking probes.

21. The method of claim 20, further comprising the step of repositioning the placement rod proximate the tracking probe for removing the tracking probe from the structure.

22. The method of claim 21, further comprising the steps of magnetically re-coupling the placement rod to the tracking probe, decoupling the magnetic attraction between the driving and tracking probes, and removing the tracking probe form the structure.

23. The method of claim 19, further comprising the step of pumping a fluid between the pulse echo ultrasonic sensor of the tracking probe and the second surface of the structure to couple inspection signals transmitted into the structure from the pulse echo ultrasonic sensor and reflected inspection signals received at the pulse echo ultrasonic sensor from the structure.

24. The method of claim 19, further comprising the steps of:
communicating the reflected inspection signals to a processing element of an ultrasonic test system; and
determining bondline thickness based on the reflected inspection signals reflected from the near and far sides of a bondline of the structure.

* * * * *